(12) United States Patent
Gilis et al.

(10) Patent No.: US 6,663,901 B1
(45) Date of Patent: Dec. 16, 2003

(54) PELLETS HAVING A CORE COATED WITH AN ANTIFUNGAL AND A POLYMER

(75) Inventors: Paul Marie Victor Gilis, Beerse (BE); Valentin Florent Victor De Conde, Lommel (BE); Roger Petrus Gerebern Vandecruys, Westerlo (BE)

(73) Assignee: Janssen Pharmaceutical N.V., Beerse (BE)

( * ) Notice: Subject to any disclaimer, the term of this patent is extended or adjusted under 35 U.S.C. 154(b) by 0 days.

(21) Appl. No.: 09/582,551

(22) PCT Filed: Jul. 9, 1999

(86) PCT No.: PCT/EP99/04928

§ 371 (c)(1), (2), (4) Date: Jun. 27, 2000

(87) PCT Pub. No.: WO00/03697

PCT Pub. Date: Jan. 27, 2000

(30) Foreign Application Priority Data

Jul. 17, 1998 (EP) .............................. 98202408

(51) Int. Cl.[7] .................................. A61K 9/62

(52) U.S. Cl. ................ 424/494; 424/456; 424/461; 424/490; 427/213

(58) Field of Search ................. 424/456, 461, 424/490, 494; 427/213

(56) References Cited

U.S. PATENT DOCUMENTS 5,633,015 A * 5/1997 Gilis et al. ............... 424/490

FOREIGN PATENT DOCUMENTS

| WO | WO 94/05263 | 3/1994 |
|---|---|---|
| WO | WO 98/00116 | 1/1998 |
| WO | WO 98/42318 | 10/1998 |

* cited by examiner

*Primary Examiner*—Jyothsna Venkat
(74) *Attorney, Agent, or Firm*—Woodcock Washburn LLP

(57) ABSTRACT

The present invention is concerned with pellets comprising a 710–1180 μm (16–25 mesh) sugar core, a coating film of a water-soluble polymer and an antifungal agent, and a seal coating layer wherein the residual concentration of dichloromethane is below 600 ppm; pharmaceutical dosage forms comprising said pellets and a method of preparing said pellets.

2 Claims, No Drawings

PELLETS HAVING A CORE COATED WITH AN ANTIFUNGAL AND A POLYMER

CROSS REFERENCE TO RELATED APPLICATIONS

This application is a National Stage application under 35 U.S.C. §371 of PCT/EP99/04928 filed Jul. 9, 1999, which claims priority from EP 98.202.408.5, filed Jul. 17, 1998.

The present invention is concerned with novel pellets of itraconazole, a process for preparing said pellets, and oral dosage forms comprising a therapeutically effective amount of such pellets.

The development of efficaceous pharmaceutical compositions of azole antifungals such as itraconazole is hampered considerably by the fact that said antifungals are only very sparingly soluble in water. The solubility and bioavailability of said compounds can be increased by complexation with cyclodextrins or derivatives thereof as described in WO-85/02767 and U.S. Pat. No. 4,764,604.

In WO-94/05263, published on Mar. 17, 1994, there are disclosed beads having a 25–30 mesh sugar core (600–710 µm) coated with an azole antifungal, more particularly itraconazole (or saperconazole), and a polymer, more particularly, hydroxypropyl methylcellulose. Finished with a sealing film coat, such drug coated cores are referred to as beads. About 460 mg beads, equivalent to about 100 mg itraconazole, are filled into a hard-gelatin capsule (size 0) suitable for oral administration. The capsules are commercially available in many countries under the Trademark Sporanox™. The azole antifungal is easily released from the surface of the coated beads, which leads to improved bioavailability over previously known oral dosage forms of azole antifungals.

The preparation of coated beads as described in WO-94/05263 requires special techniques and special equipment in a purpose-built plant. Indeed, the beads described in the prior art are prepared in a quite complex manner requiring a lot of manipulation steps. First, a drug coating solution is prepared by dissolving appropriate amounts of the antifungal agent and a hydrophilic polymer, preferably hydroxypropyl methylcellulose (HPMC), into a suitable solvent system. A suitable solvent system comprises a mixture of methylene chloride and an alcohol. Said mixture should comprise at least 50% by weight of methylene chloride acting as a solvent for the drug substance. As hydroxypropyl methylcellulose does not dissolve completely in methylene chloride, at least 10% alcohol has to be added. Subsequently, the 25–30 mesh sugar cores are drug-coated in a fluidized bed granulator equipped with a bottom spray insert. Not only should the spraying rate be regulated carefully, but also temperature control in the fluidized bed granulator is crucial. Hence, this process requires a lot of control in order to obtain a good quality product reproducibly. Further, this technique requires the adequate resolution of the issue of residual organic solvents, such as methylene chloride and methanol or ethanol, being present in the coating. In order to remove any solvents which may remain in the drug-coated intermediate product, a drying step in vacuo is required. Subsequently, a seal coating is applied to the dried drug coated cores.

WO-94/05263 explains that the size of the cores is of considerable importance. On the one hand, if the cores are too large, there is less surface area available for applying the drug coating layer, which results in thicker coating layers. This raises problems in the manufacturing process as an intensive drying step is needed to reduce residual solvent levels in the coating layer. The intense drying conditions may adversely affect drug dissolution from the pellets and should therefore be controlled extremely well during the manufacturing process. On the other hand, small cores have a larger total surface available for coating resulting in thinner coating layers. Consequently a far less intensive drying step can be used to decrease residual solvents levels. Cores which were too small, e.g. 500–600 µm (30–35 mesh) cores, however, had the disadvantage of showing considerable tendency to agglomerate during the coating process. Therefore, it was concluded that 600–710 µm (25–30 mesh) cores represented the optimum size where neither agglomeration nor an intensive drying step constrained the process.

It would be highly desirable to have access to pharmaceutical dosage forms comprising drug coated cores wherein the cores are relatively large, 710–1180 µm (25–16 mesh), in particular 710–1000 µm (25–18 mesh) and especially 710–850 µm (25–20 mesh), and wherein the residual solvent levels in said drug coated cores are within the limits set out by the International Conference on Harmonisation (ICH) [ICH Topic Q3C Impurities.: Residual Solvents (CPMP/ICH/283/95) in force as of March 1998]. Therein, dichloromethane and methanol are both considered to be Class 2 solvents whose presence in pharmaceutical products should be limited; their respective Permitted Daily Exposure (PDE) is 6 mg/day and 30 mg/day; their respective concentration limits in pharmaceutical dosage forms are 600 ppm and 3000 ppm.

As mentioned previously, attaining these low residual solvent levels in beads with a relatively large core and a relatively thick drug/polymer coating layer is difficult. As the drug coat grows thicker, it takes longer for the residual solvent to diffuse outwardly. The rate of diffusion of a solute being proportional to its concentration gradient, it follows that lowering pressure should help to reduce the residual solvent levels.

However, the lower pressure at the same time dimishes the efficiency of heat transfer to the drug coated beads when conventional heating techniques are used, and thus, the evaporation of the residual solvents is slowed down. The present invention provides a method of efficiently conveying heat to the drug coated cores in a low pressure environment, thus enabling one to obtain drug coated cores that satisfy the above-mentioned guidelines issued by ICH. The method for the first time allows one to obtain relatively large beads complying with the newest international limits on residual solvents in pharmaceutical products.

Itraconazole or (±)-cis-4-[4-[4-[4-[[2-(2,4-dichlorophenyl)-2-(1H-1,2,4-triazol-1-methyl)-1,3-dioxolan-4-yl]methoxy]phenyl]-1-piperazinyl]phenyl]-2,4-dihydro-2-(1-methylpropyl)-3H-1,2,4-triazol-3-one, is a broadspectrum antifungal compound developed for oral, parenteral and topical use and is disclosed in U.S. Pat. No. 4,267,179. Its difluoro analog, saperconazole or (±)-cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methoxypropyl)-3H-1,2,4-triazol-3-one, has improved activity against Aspergillus spp. and is disclosed in U.S. Pat. No. 4,916,134. Both itraconazole and saperconazole consist of a mixture of four diastereoisomers, the preparation and utility of which is disclosed in WO-93/19061: the diastereoisomers of itraconazole and saperconazole are designated [2R-[2α,4α,4(R*)]], [2R-[2α,4α,4(S*)]], [2S-[2α,4α,4(S*)]] and [2S-[2α,4α,4(R*)]]. The term "itraconazole" as hereinafter is to be interpreted broadly and comprises the free base form and the pharmaceutically acceptable addition salts of itraconazole, or of one of its stereoisomers, or of a mixture of two or three of its stereoisomers. The preferred itraconazole compound is the (±)-(cis) form of the free base form. The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxy-propanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

It may be remarked that therapeutically effective plasm levels of itraconazole can be maintained easily for at least 24 hours as its half-life is sufficiently high. The condition is that the itraconazole must reach the plasm. The absorption of dissolved itraconazole from the stomach is in itself not a problem. Thus, there is no need for a sustained release dosage form of itraconazole, an immediate release form will do just as well. In other words, the main problem with the administration of itraconazole in therapeutically effective amounts is in the first place concerned with ensuring that a sufficient amount of itraconazole remains in solution sufficiently long to allow it to get into the circulation, and does not convert into a form that is not readily bioavailable, in particular crystalline itraconazole (which is formed when itraconazole precipitates in an aqueous medium).

Unexpectedly, it has now been found that pellets larger than those described in WO-94/05263, and wherein the residual solvent levels are within the guidelines of ICH, can be manufactured conveniently after all. In these novel pellets, the residual solvent levels are reduced by irradiating the pellets in vacuo with microwave or radiofrequency radiation. Probably, the improved efficacy of the drying process using radiation may be explained by the superior heat transfer; whereas conventional heating relies on energy exchange upon collison of particles, irradiation directly transfers the energy required to evaporate the solvent to the drug coated particle.

The present invention also provides pharmaceutical compositions of itraconazole and a water-soluble polymer which can be administered to a patient suffering from a fungal infection. The dosage forms comprise a therapeutically effective amount of novel pellets as described in detail hereunder.

In particular the present invention is concerned with pellets which comprise (a) a central, rounded or spherical core having a diameter of about 710–1180 $\mu$m (25–16 mesh), in particular 710–1000 $\mu$m (25–18 mesh) and especially 710–850 $\mu$m (25–20 mesh), (b) a coating film of a water-soluble polymer and an antifungal agent and (c) a seal-coating polymer layer, characterized in that the residual solvent levels in said pellets are within the limits set out by the International Conference on Harmonisation (ICH) [ICH Topic Q3C Impurities: Residual Solvents (CPMP/ICH/283/95) in force as of March 1998], that is, the concentration of dichloromethane in said pellets is less than 600 ppm, preferably less than 300 ppm and most preferably less than 250 ppm.

The alcoholic co-solvent that is necessary for applying the drug coat layer to the cores is preferably ethanol, a Class 3 solvent, rather than methanol, a Class 2 solvent, even though ethanol has a higher boiling point and a slightly higher latent heat evaporation and thus requires a larger energy input than methanol.

Cores of the dimensions mentioned herein can be obtained by sieving through nominal standard test sieves as described in the CRC Handbook, $64^{th}$ ed., page F-114. Nominal standard sieves are characterized by the mesh/hole width ($\mu$m), DIN 4188 (mm), ASTM E 11-70 (No), Tyler® (mesh) or BS 410 (mesh) standard values. Throughout this description and the claims, particle sizes are designated by reference to the mesh/hole width in $\mu$m and to the corresponding Sieve No in the ASTM E11-70 standard.

Materials suitable for use as cores in the pellets according to the present invention are manifold, provided that said materials are pharmaceutically acceptable and have appropriate dimensions (about 16–25 mesh, preferably about 20–25 mesh) and firmness. Examples of such materials are polymers e.g. plastic resins; inorganic substances, e.g. silica, glass, hydroxyapatite, salts (sodium or potassium chloride, calcium or magnesium carbonate) and the like; organic substances, e.g. activated carbon, acids (citric, fumaric, tartaric, ascorbic and the like acids), and saccharides and derivatives thereof. Particularly suitable materials are saccharides such as sugars, oligosaccharides, polysaccharides and their derivatives, for example, glucose, rhamnose, galactose, lactose, sucrose, mannitol, sorbitol, dextrin, maltodextrin, cellulose, microcrystalline cellulose, sodium carboxymethyl cellulose, starches (maize, rice, potato, wheat, tapioca) and the like saccharides.

A particularly preferred material suitable for use as cores in the pellets according to the present invention is represented by 20–25 mesh sugar cores (USP 22/NF XVII, p. 1989) which consist of 62.5%–91.5% (w/w) sucrose, the remainder being starch and possibly also dextrines, and which are pharmaceutically inert or neutral. Consequently, these cores are also known in the art as neutral pellets.

Pellets obtainable from 20–25 mesh sugar cores comprise approximately, by weight based on the total weight of the pellet: (a) 35 to 60 percent core material; (b) 23 to 37 percent water-soluble polymer; (c) 15 to 25 percent antifungal agent; and (d) 2 to 4 percent seal coating polymer.

The water-soluble polymer in the pellets according to the present invention is a polymer that has an apparent viscosity of 1 to 100 mPa.s when dissolved in a 2% aqueous solution at 20° C. solution. For example, the water-soluble polymer can be selected from the group comprising alkylcelluloses such as methylcellulose,
hydroxyalkylcelluloses such as hydroxymethylcellulose, hydroxyethylcellulose, hydroxypropylcellulose and hydroxybutylcellulose,
hydroxyalkyl alkylcelluloses such as hydroxyethyl methylcellulose and hydroxypropyl methylcellulose,
carboxyalkylcelluloses such as carboxymethylcellulose,
alkali metal salts of carboxyalkylcelluloses such as sodium carboxymethylcellulose,
carboxyalkylalkylcelluloses such as carboxymethylethylcellulose,
carboxyalkylcellulose esters,
starches,
pectines such as sodium carboxymethylamylopectine,
chitine derivates such as chitosan,
polysaccharides such as alginic acid, alkali metal and ammonium salts thereof, carrageenans, galactomannans, tragacanth, agar-agar, gummi arabicum, guar gummi and xanthan gummi, polyacrylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate,
polyalkylene oxides such as polyethylene oxide and polypropylene oxide and copolymers of ethylene oxide and propylene oxide.

Non-enumerated polymers which are pharmaceutically acceptable and have appropriate physico-chemical properties as defined hereinbefore are equally suited for preparing drug coated cores according to the present invention.

The drug coating layer preferably comprises a water-soluble polymer such as hydroxypropyl methylcellulose (Methocel®, Pharmacoat®), methacrylate (Eudragit E®), hydroxypropylcellulose (Klucel®), or a polyvidone. Preferred water-soluble polymers are hydroxypropyl methylcelluloses or HPMC. Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule. Hydroxypropyl methylcellulose is the United States Adopted Name for hypromellose (see Martindale, The Extra Pharmacopoeia, 29th edition, page 1435). Preferably hydroxypropyl methylcellulose with low viscosity, i.e. about 5 mPa.s, is used, e.g. hydroxypropyl methylcellulose 2910 5 mPa.s. In the four digit number "2910", the first two digits represent the approximate percentage of methoxyl groups and the third and fourth digits the approximate percentage composition of hydroxypropoxyl groups. 5 mPa.s is a value indicative of the apparent viscosity of a 2% aqueous solution at 20° C.

Suitable HPMC include those having a viscosity from about 1 to about 100 mPa.s, in particular form about 3 to about 15 mPa.s, preferably about 5 mPa.s The most preferred type of HPMC having a viscosity of 5 mPa.s., is the commercially available HPMC 2910 5 mPa.s.

Preferred antifungal agents for use as drugs in said drug coating layer are lipophilic azole antifungals, in particular itraconazole. Optimum dissolution results are obtained when the drug substance is present in a solid dispersion or solution state as can be confirmed by differential scanning calorimetry.

The weight-by-weight ratio of drug: polymer is in the range of 1:1 to 1:5, preferably 1:1 to 1:3. In the case of (itraconazole):(HPMC 2910 5 mPa.s), said ratio may range from about 1:1 to about 1:2, and optimally is about 11.5 (or 2:3). The weight by weight ratio of itraconazole to other water-soluble polymers may be determined by a person skilled in the art by straightforward experimentation. The lower limit is determined by practical considerations. Indeed, given the therapeutically effective amount of itraconazole (from about 50 mg to about 300 mg, preferably about 200 mg per day), the lower limit of the ratio is determined by the maximum amount of mixture that can be processed into one dosage form of practical size. When the relative amount of water-soluble polymer is too high, the absolute amount of mixture needed to reach the therapeutic level will be too high to be processed into one capsule or tablet. Capsules of size 0 can contain about 460 mg, minimally 35% of which comprises the cores, the remaining 65% (300 mg) being the maximum amount of antifungal and polymer. Consequently, the lower limit of the amount of itraconazole over hydroxypropyl methyl cellulose will be about 1:5 (50 mg itraconazole+250 mg water-soluble polymer).

On the other hand, if the ratio is too high, this means the amount of itraconazole is relatively high compared to the amount of water-soluble polymer, then there is the risk that the itraconazole will not dissolve sufficiently in the water-soluble polymer, and thus the required bioavailability will not be obtained. The 1:1 upper limit is determined by the fact that it was observed that above said ratio not all of the itraconazole had dissolved in the HPMC. It will be appreciated that the upper limit of 1:1 may be underestimated for particular water-soluble polymers. Since this can be established easily but for the experimentation time involved, solid dispersions wherein the ratio drug:polymer ratio is larger than 1:1 are also meant to be comprised within the scope of the present invention.

The drug coating layer of the pellets as described hereinabove may further comprise one or more pharmaceutically acceptable excipients such as, for example, plasticizers, flavors, colorants, preservatives and the like. Said excipients should be inert, in other words, they should not show any degradation or decomposition under the manufacturing conditions.

In the current itraconazole:HPMC 2910 5 mPa.s formulations, the amount of plasticizer is preferably small, in the order of 0% to 15% (w/w), preferably less than 5% (w/w), most preferably 0% (w/w). With other water-soluble polymers though, plasticizers may be employed in different, often higher amounts. Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molcular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

A seal coating polymer layer is applied to the drug coated cores to prevent sticking of the pellets which would have the undesirable effect of a concomitant decrease of the dissolution rate and of the bioavailability. Preferably, a thin layer of polyethylene glycol (PEG), in particular polyethylene glycol 20000 (Macrogol 20000) is used as a seal coating polymer layer.

The preferred pellets comprise approximately: (a) 40 to 43 percent sugar core; (b) 30 to 35 percent hydroxypropyl methylcellulose 2910 5 mPa.s; (c) 20 to 25 percent itraconazole; and (d) 2 to 4 percent polyethylene glycol 20000.

In addition, the pellets according to the present invention may further contain various additives such as thickening agents, lubricants, surfactants, preservatives, complexing and chelating agents, electrolytes or other active ingredients, e.g. antiinflammatory agents, antibacterials, disinfectants or vitamins.

The pellets according to the present invention can conveniently be formulated into various pharmaceutical dosage forms. Suitable dosage forms comprise an effective antifungal amount of pellets as described hereinbefore. Preferably, the pellets are filled in hard-gelatin capsules such that an amount of, for example, 100 mg of the active ingredient is available per dosage form. For example, hard-gelatin capsules of size 0 are suitable for formulating pellets comprising 20 to 25 percent by weight itraconazole or saperconazole, equivalent to about 100 mg active ingredient.

The pellets according to the present invention are conveniently prepared in the following manner. A drug coating solution is prepared by dissolving into a suitable solvent system appropriate amounts of an antifungal agent and a water-soluble polymer. A suitable solvent system comprises a mixture of methylenechloride and an alcohol, preferably ethanol which may be denatured, for example, with butanone. Said mixture should comprise at least 50% by weight of methylenechloride acting as a solvent for the drug substance. As hydroxypropyl methylcellulose does not dissolve completely in methylenechloride, at least 10% alcohol has to be added. Preferably a relatively low ratio of methylenechloride/alcohol is used in the coating solution, e.g. a ratio methylene-chloride/ethanol ranging from 75/25 (w/w) to 55/45 (w/w), in particular about 60/40 (w/w). The amounts of solids, i.e. antifungal agent and water-soluble polymer, in the drug coating solution may range from 7 to 10% (w/w) and preferably is about 8.7%.

The drug coating process (on an industrial scale) is conveniently conducted in a fluidized bed granulator (e.g. Glatt type WSG-30 or GPCG-30) equipped with a Wurster bottom spray insert (e.g. an 18 inch Wurster insert). Laboratory scale process development can be performed on a Glatt type WSG-1 with a 6 inch Wurster bottom insert. Obviously, the process parameters depend on the equipment used.

The spraying rate should be regulated carefully. Too low a spraying rate can cause some spray drying of the drug coating solution and result in a loss of product. Too high a spraying rate will cause overwetting with subsequent agglomeration. Agglomeration being the most serious problem, lower spraying rates may be used initially, to be increased as the coating process proceeds and the pellets grow larger.

The atomizing air pressure with which the drug coating solution is applied also influences the coating performance. Low atomizing air pressure results in the formation of larger droplets and an increased tendency toward agglomeration. High atomizing air pressure could conceivably carry the risk of spray drying of the drug solution, but this was found not to be a problem. Consequently, atomizing air pressure may be set at nearly maximum levels.

Fluidizing air volume can be monitored by operating the exhaust air-valve of the apparatus and should be set in such a manner that optimum pellet circulation is obtained. Too low an air volume will cause insufficient fluidization of the pellets; too high an air volume will interfere with the pellet circulation due to countercurrent air streams developing in the apparatus. In the present process optimum conditions were obtained by opening the exhaust air valve to about 50% of its maximum and gradually increasing the opening thereof to about 60% of the maximum as the coating process proceeded.

The coating process is advantageously conducted by employing an inlet-air temperature ranging from about 50° C. to about 55° C. Higher temperatures may speed up the process but have the disadvantage that solvent evaporation is so rapid that the coating liquid is not spread uniformly on the surface of the pellets resulting in the formation of a drug coating layer with high porosity. As the bulk volume of the coated pellets increases, drug dissolution may decrease significantly to unacceptable levels. Obviously, the optimum process temperature will further depend on the equipment used, the nature of the core and the antifungal agent, the batch volume, the solvent and the spraying rate.

Parameter settings for optimum coating results are described in more detail in the example hereinafter. Running the coating process under those conditions was found to yield very reproducible results.

In order to reduce residual solvent levels in the drug coating layer, the drug coated cores can conveniently be dried in a microwave vacuum apparatus, for example as described in U.S. Pat. No. 4,882,851 by The Fitzpatrick Co. of Elmhurst, Ill. USA. Good results may be obtained using a vacuum ranging from about 150–400 mbar (15–40 kpa), preferably 200–300 mbar (20–30 kPa). Microwave (or radiofrequency) power may applied continuously, but is preferably pulsed as is described in U.S. Pat. No. 5,440,104. After drying, the drug coated cores may be sieved.

The seal coating polymer layer is applied to the drug coated cores in the fluidized bed granulator with Wurster bottom spray insert. The seal coating solution can be prepared by dissolving an appropriate amount of a seal coating polymer into a suitable solvent system. Such a system, is, e.g. a mixture of methylene chloride and an alcohol, preferably ethanol which may be denatured with, for example, butanone. The ratio of methylene chloride/alcohol used may be similar to the ratio used in the drug coating process and thus can range from about 75/25 (w/w) to about 55/45 (w/w) and in particular is about 60/40 (w/w). The amount of seal coating polymer in the seal coating spraying solution may range from 7 to 12% (w/w) and preferably is about 10%. The seal coating spraying solution is advantageously stirred during the seal coating process. The parameter setting for conducting this last step is essentially similar to that used in the drug coating process. Appropriate conditions are described in more detail in the example hereinafter.

Both the drug coating process and the seal coating process are preferably conducted under an inert atmosphere of e.g. nitrogen. The coating equipment should preferably be grounded and provided with an appropriate solvent recovery system containing an efficient condensing system.

The drug coated and seal coated pellets may be filled in hard-gelatin capsules using standard automatic capsule filling machines. Suitable earthing and de-ionisation equipment can advantageously prevent development of electrostatic charges.

Capsule filling speed may influence weight distribution and should be monitored. Good results are obtained when operating the equipment at about 75% to 85% of the maximum speed and in many cases when operating at full speed.

Pharmaceutical dosage forms for oral administration such as tablets comrising the drug coated cores (preferably without a seal coat) are also envisaged. They can be produced by conventional tabletting techniques with conventional ingredients or excipients and with conventional tabletting machines. In addition, they can be produced at low cost. The shape of the tablets may be round, oval or oblong. In order to facilitate the swallowing of large dosage forms by a patient, it is advantageous to give the tablets an appropriate shape. Tablets that can be swallowed comfortably are therefore preferably elongated rather than round in shape. Especially preferred are biconvex oblate tablets. As discussed hereunder in more detail, a film coat on the tablet further contributes to the ease with which it can be swallowed.

Tablets that give an immediate release of antifungal agent upon oral ingestion and that have good bioavailability are designed in such a manner that the tablets disintegrate rapidly in the stomach (immediate release) and that the dug coated cores which are liberated thereby are kept away from one another so that they do not coalesce. Thus, local concentrations of antifungal agent remain low and there is little chance that the drug will precipitate (bioavailability). The desired effect can be obtained by distributing said drug coated cores homogeneously throughout a mixture of a disintegrant and a diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and preferably is about 7 to 9%, in particular about 8.5% (w/w). This amount tends to be larger than usual in tablets in order to ensure that the drug coated cores are spread over a large volume of the stomach contents upon ingestion. Because disintegrants by their nature yield sustained release formulations when employed in bulk, it is advantageous to dilute them with an inert substance called a diluent or filler.

A variety of materials may be used as diluents or fillers. Examples are spray-dried or anhydrous lactose, sucrose, dextrose, mannitol, sorbitol, starch, cellulose (e.g. microcrystalline cellulose Avicel™), dihydrated or anhydrous dibasic calcium phosphate, and others known in the art, and mixtures thereof. Preferred is a commercial spray-dried mixture of lactose monohydrate (75%) with microcrystalline cellulose (25%) which is commercially availble as Microcelac™. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I (micronized), most preferably hydrogenated, deodorized Cottonseed oil (commercially available from Karlshamns as Akofine NF™ (formerly called Sterotex™)). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but when used the coloring agent can be present in an amount up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth. The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated to improve taste, to provide ease of swallowing and an elegant appearance. Many suitable polymeric film-coating materials are known in the art. A preferred film-coating material is hydroxypropyl methylcellulose HPMC, especially HPMC 2910 5 mPa.s. Other suitable film-forming polymers also may be used herein, including, hydroxypropylcellulose, and acrylatemethacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In immediate release tablets according to the invention, the film coat is small and in terms of weight accounts for less than about 3.5% (w/w) of the total tablet weight.

Preferred dosage forms are those wherein the weight of the drug coated cores ranges from 40% to 60% of the total weight of the total dosage form, that of the diluent ranges from 20 to 40%, and that of the disintegrant ranges from 3 to 10%, the remainder being accounted for by one or more of the excipients described hereinabove.

As an example of an oral dosage form comprising 100 mg of itraconazole, the following formula may be given:

sugar cores 710–850 $\mu$m (20–25 mesh/192 mg)

itraconazole (100 mg)

HPMC 2910 5 mPa.s (150 mg)

microcrystalline cellulose (452 mg)

hydrogenated vegetable oil Type I micronized (6 mg).

Using the process parameters described above, a convenient, reproducible manufacturing method for preparing pellets comprising a 20–25 mesh core, a drug coat layer of an antifungal agent and a water-soluble polymer and a thin seal-coating polymer layer can be obtained. Pharmacokinetic studies show that the thus obtained pellets have excellent dissolution and bioavailability properties.

Preferred dosage forms according to the present invention are those from which at least 85% of the available itraconazole dissolves within 60 minutes when a dosage form equivalent to 100 mg itraconazole is tested as set forth in USP test <711> in a USP-2 dissolution apparatus under conditions at least as stringent as the following: 900 mL artificial gastric juice (1.8 g NaCl, 6.3 mL concentrated HCl and 9 g polysorbate 20 diluted with distilled water to 900 mL), 37° C. with paddles turning at 100 rpm. Capsules complying with the preceding definition can be said to have Q>85% (60'). Preferably, capsules according to the present invention will dissolve faster and have Q>85% (30').

EXAMPLE a) Itraconazole Spraying Solution 1

A stainless steel vessel (10 l) was charged with methylene chloride (4.722 kg) and ethanol (3.147 kg) through a filter (5 l). Itraconazole (300 g) and hydroxypropyl methylcellulose 2910 5 mPa.s (450 g) were added while stirring. Stirring of the itraconazole spraying solution was continued until complete dissolution was obtained.

b) Seal-coating Spraying Solution

A stainless steel vessel (5 L) was charged with methylene chloride (291.6 g) and ethanol (194.4 g) while stirring. Polyethylene glycol 20000 (Macrogol 20000) (54 g) was added and the solution was stirred until homogeneous.

c) Drug Coating Process

A fluidized-bed granulator (Glatt, type WSG 1) equipped with a 6 inch Wurster (bottom spray) insert was loaded with 710–850 $\mu$m (20–25 mesh) sugar cores (575 g). The cores were warmed with dry air of about 50° C. The fluidizing air volume was controlled by opening the exhaust air valve to approximately 45% of its maximum. The itraconazole spraying solution was then sprayed on the cores moving in the apparatus. The solution was sprayed at an delivery rate of about 15 g.min$^{-1}$ at an atomizing air pressure of about 1.9–2.0 bar (0.19–0.2 MPa). When the spraying process was completed, the coated cores were dried by further supplying dry air of 60° C. for about 2 minutes. The coated cores were then allowed to cool in the apparatus by supplying dry air of 20–25° C. for about 10 to 20 minutes. The apparatus was emptied, the drug coated cores were collected and stored in a stainless steel drum.

d) Microwave Drying

In order to reduce residual solvent levels, the coated cores were then transferred to a vacuum processor (Gral 25) equiped with a microwave generator (Collette) and irradiated during 1 hour at 25 kPa and 1 to 1.2 kW. The pellets were stirred every three minutes so as to obtain homogenous drying.

e) Seal-coating Process

The dried coated cores were introduced again into the fluidized-bed granulator equipped with the Wurster insert and warmed with dry air of about 50° C. The seal-coating spraying solution was then sprayed on the coated cores moving in the apparatus. The solution was sprayed at an delivery rate of about 15 g.min$^{-1}$, at an atomizing air pressure of about 1.6 bar (0.16 MPa). When the spraying process was completed, the pellets were dried by further supplying dry air of 60 ° C. for 4 min. The coated cores were then allowed to cool in the apparatus by supplying dry air of 20°–25° C. for about 5 to 15 minutes. The pellets were removed from the apparatus and stored in suitable containers.

f) Capsule Filling

The drug coated pellets were filled into hard-gelatin capsules (size 0) using standard automatic capsule filling machines (e.g. Model GFK-1500, Höffliger and Karg. Germany). In order to obtain capsules with good weight distribution, capsule filling speed was reduced to about 75–85% of the maximum speed. Each capsule received approximately 460 mg pellets, equivalent to about 100 mg itraconazole. Using the process parameters described above, itraconazole 100 mg hard-gelatin capsules were obtained which met all the requirements, in particular the dissolution specifications.

g) Dissolution Properties

In-vitro dissolutions studies will be performed on the 100 mg capsule formulation. The medium was 900 ml of artificial gastric juice (1.8 g NaCl, 6.3 mL concentrated HCl and 9 g polysorbate 20 diluted with distilled water to 900 mL) at 37° C. in Apparatus 2 (USP 23, <711> Dissolution, pp. 1791–1793) (paddle, 100 rpm).

h) Tablet Formulation

Following the procedure described hereinbefore a batch of pellets was prepared having a weight-by-weight ratio of (itraconazole):(HPMC 2910 5 mPa.s)=1:1.5. 460 mg of pellets (comprising 192 mg sugar cores 710–850 $\mu$m; 100 mg itraconazole and 150 mg polymer) were blended with 452 mg of microcrystalline cellulose and 6 mg of hydrogenated vegetable oil type I (micronized) and compressed on an Exenterpress Courtois 27, yielding a tablet having a nominal weight of 900 mg.

i) Comparison with Pellets Dried Using Conventional Heating

A batch of pellets as prepared in paragraph c) was tested for residual dichloromethane levels before drying and after drying at 60° C. for 8, 24, 32 and 48 hours in a vacuum tumble-drier (25 kPa).

| Condition | Dichloromethane concentration (ppm) |
|---|---|
| before drying | 2,550 |
| 60° C., 8 h | 2,160 |
| 60° C., 24 h | 1,710 |
| 60° C., 32 h | 1,530 |
| 60° C., 48 h | 1,310 |

Samples of the pellets dried following the procedure of paragraph d) yielded the following data.

| Condition | Dichloromethane concentration (ppm) |
|---|---|
| before drying | 2,550 |
| 1 h | <250 |

What is claimed is:

1. A process for preparing pellets, each of said pellets comprising a central, rounded or spherical core having a diameter from about 710 to about 1180 $\mu$m (16–25 mesh);

a coating film of a water-soluble polymer and an antifungal agent, and a seal-coating polymer layer, wherein the process comprises
  a) coating sugar cores by spraying them with a solution of an antifungal agent and a water-soluble polymer in an organic solvent comprising methylene chloride and an alcohol in a fluidized-bed granulator equipped with a bottom spray insert;
  b) drying the resulting coated cores in vacuo by irradiating said cores with microwave or radiofrequency radiation; and
  c) seal-coating the dried cores by spraying them with a solution of a seal-coating polymer in an organic solvent comprising methylene chloride and an alcohol in a fluidized-bed granulator equipped with a bottom spray insert,
  wherein said pellets have a residual concentration of dichloromethane of less than 600 ppm.

2. The process of claim 1, wherein the alcohol is ethanol.

* * * * *